(12) United States Patent
Livache et al.

(10) Patent No.: US 11,953,483 B2
(45) Date of Patent: Apr. 9, 2024

(54) METHOD FOR DETERMINING A POTENTIAL POISONING OF A SENSOR OF AN ELECTRONIC NOSE BY A VOLATILE COMPOUND

(71) Applicant: ARYBALLE, Grenoble (FR)

(72) Inventors: Thierry Livache, Jarrie (FR); Cyril Herrier, Grenoble (FR); Romain Dubreuil, Grenoble (FR)

(73) Assignee: ARYBALLE, Grenoble (FR)

(*) Notice: Subject to any disclaimer, the term of this patent is extended or adjusted under 35 U.S.C. 154(b) by 231 days.

(21) Appl. No.: 17/442,201

(22) PCT Filed: Mar. 25, 2020

(86) PCT No.: PCT/EP2020/058402
§ 371 (c)(1),
(2) Date: Sep. 23, 2021

(87) PCT Pub. No.: WO2020/193647
PCT Pub. Date: Oct. 1, 2020

(65) Prior Publication Data
US 2022/0187263 A1 Jun. 16, 2022

(30) Foreign Application Priority Data
Mar. 28, 2019 (FR) ........................................ 1903287

(51) Int. Cl.
*G01N 33/00* (2006.01)
(52) U.S. Cl.
CPC .................................. *G01N 33/007* (2013.01)

(58) Field of Classification Search
CPC .......................... G01N 33/0047; G01N 33/007
See application file for complete search history.

(56) References Cited

U.S. PATENT DOCUMENTS

2002/0146352 A1* 10/2002 Wang ..................... G01N 27/16
422/94
2002/0168772 A1* 11/2002 Lloyd ................... G01N 33/007
436/152

(Continued)

FOREIGN PATENT DOCUMENTS

DE 102009038277 A1 * 3/2011 ........... G01N 33/007
FR 3071061 A1 3/2019

(Continued)

OTHER PUBLICATIONS

Search Report issued in French Patent Application No. 1903287 dated Dec. 16, 2019.

(Continued)

*Primary Examiner* — Natalie Huls
(74) *Attorney, Agent, or Firm* — Pearne & Gordon LLP

(57) ABSTRACT

A method determines a potential poisoning of a sensor of an electronic nose by a volatile compound following an exposure of the sensor to a gaseous sample including at least this volatile compound. If there is poisoning, the method determines whether the sensor is still functional such that the sensor is still capable of carrying out one or a plurality of reliable measurements, or on the contrary, whether the sensor is saturated and must no longer be used. The method may be used with any type of electronic nose.

14 Claims, 2 Drawing Sheets

(56) References Cited

U.S. PATENT DOCUMENTS

2013/0130243 A1    5/2013  Livache et al.
2014/0342459 A1*  11/2014  Berndt .................. G01N 31/10
                                                     422/83
2020/0256793 A1*   8/2020  Hou-Broutin ...... G01N 33/0031

FOREIGN PATENT DOCUMENTS

JP       2016075532 A  *  5/2016  ........... G01N 33/497
WO       2004010085 A1    1/2004

OTHER PUBLICATIONS

International Search Report for Application No. PCT/EP2020/058402 dated Jun. 4, 2020.
Written Opinion for PCT/EP2020/058402 dated Jun. 4, 2020.
Haugen, John-Erik, et al., "A calibration method for handling the temporal drift of solid state gas-sensors", Analytica Chimica Acta, Feb. 29, 2000, pp. 23-39, vol. 407, No. 1-2, XP055152962.
Distante, C., et al., "Support vector machines for olfactory signals recognition", Sensors and Actuators B: Chemical, Elsevier BV, NL, Jan. 1, 2003, pp. 30-39, vol. 88, No. 1, XP004395009.
Brenet, Sophie, et al., "Highly-Selective Optoelectronic Nose Based on Surface Plasmon Resonance Imaging for Sensing Volatile Organic Compounds", Analytical Chemistry, 2018, 90, pp. 9879-9887.

* cited by examiner

METHOD FOR DETERMINING A POTENTIAL POISONING OF A SENSOR OF AN ELECTRONIC NOSE BY A VOLATILE COMPOUND

This is the National Stage of PCT international application PCT/EP2020/058402, filed on Mar. 25, 2020 entitled "METHOD FOR DETERMINING A POTENTIAL POISONING OF A SENSOR OF AN ELECTRONIC NOSE BY A VOLATILE COMPOUND", which claims the priority of French Patent Application No. 1903287 filed Mar. 28, 2019, both of which are incorporated herein by reference in their entirety.

TECHNICAL FIELD

The invention relates to the field of electronic noses.

More specifically, the invention relates to a method for determining a potential poisoning of a sensor of an electronic nose by a volatile compound following an exposure of the sensor to a gaseous sample comprising at least this volatile compound and, if there is poisoning, for determining whether the sensor is still functional, that is to say whether it is still capable of carrying out a reliable measurement, or on the contrary, whether it is saturated and must no longer be used.

The invention also relates to a computer program comprising instructions for the implementation by a computer of certain steps of this method as well as an electronic nose comprising a data processing unit for implementing said steps.

The method of the invention may be used in any type of electronic nose. However, it is of particular interest for so-called bio-inspired electronic noses, which comprise a network of sensors the sensitive portion of which (that is to say the portion of the sensors that interacts physicochemically with the volatile compounds) is functionalised by biological or biomimetic receptors, such as that described by S. Brenet et al. in *Analytical Chemistry* 2018, 90, 9879-9887.

Prior Art

Olfaction, or sense of smell, is the sense of which mammals and, particularly, human beings are provided with that makes it possible for them to detect and analyse the volatile compounds present in a gaseous medium and, particularly, ambient air.

Currently, there is a very high demand for portable instruments that are capable of mimicking olfaction. These instruments, which are called electronic noses, potentially have many applications and particularly:

in the field of health, for example to offer a substitute for the sense of smell to people suffering from a loss of smell, partial (hyposmia) or total (anosmia), or to diagnose or monitor the development of diseases that accompany the presence of odorous volatile compounds in biological fluids or in the breath, such as diabetes, certain cancers (prostate, lung, ovarian cancer, etc.) and certain microbial infections;

in the food, cosmetic and pharmaceutical industries, for example to detect possible contaminations in the manufacturing and/or distribution lines or to carry out quality controls on the raw materials or the finished products;

in the field of aromas and perfumes;

in the field of the safety of goods and people, for example to monitor sites manufacturing, storing, handling and/ or likely to be contaminated by potentially dangerous volatile materials, to detect the presence of dangerous substances such as explosives or toxic agents, or illicit substances such as drugs, or to find people buried under rubble or rockfalls; and in the field of the environment, for example for the monitoring of the quality of air or of more or less confined atmospheres, or for the surveillance and the analysis of olfactory nuisances and, particularly, of odours due to sulphur or amino volatile organic compounds, of industrial or agricultural origin.

As its biological analogue, an electronic nose mainly consists of three systems, namely:

(1) a fluidic system for transporting a gaseous sample from the outside of the electronic nose towards the inside of this nose, as well as the rinsing of the system by a neutral gas stream.

(2) a detection system that comprises a network of sensors with crossed reactivity in relation to volatile compounds present in a sample of the gaseous medium, the sensors playing the role of the olfactory receptors of the human nose; and (3) a computer system ensuring the processing of the responses emitted by the sensors in the form of signals, this system playing the role of the human brain.

The sensors of an electronic nose must satisfy a number of requirements of which that of having, in relation to volatile compounds, a significant sensitivity and a selectivity but also that of having a stability, namely that, in fixed conditions, the baseline of the sensors must remain constant or almost constant, and a reversibility, namely that the sensors must be capable of reverting to their initial state in the absence of any exposure to a volatile compound.

Yet, it is proven that certain volatile compounds such as sulphur compounds (in particular, hydrogen sulphide and thiols such as ethanethiol) and amino compounds—that are targets of interest in many fields of application of electronic noses—as well as certain compounds from cigarette smoke adsorb in a prolonged manner on the sensitive portion of the sensors that react to these compounds. This results in a modification of the surface state of the sensitive portion of the sensors with, as a consequence, a reduction of their sensitivity and, therefore, of the reproducibility of the measurements carried out by the sensors when they are exposed a plurality of times in succession to the volatile compounds in question, this reduction being all the more pronounced if the amount of volatile compounds adsorbed is high.

This is referred to as poisoning of sensors and the volatile compounds responsible for this poisoning are commonly called poisonous volatile compounds.

The poisoning even if only of a few sensors of the network of sensors of an electronic nose affects the overall performances of this nose.

Some techniques have been described to reduce this poisoning effect. Examples include the French patent application 3 071 061, which proposes to use a perfluorinated coating to reduce in a general manner the drift of the sensors that is not only related to the poisonous compounds (degradation of the sensors, humidity or environmental variation, etc.).

It happens that currently, no tool exists that makes it possible to determine whether one or more sensors of the network of sensors of an electronic nose are or are not poisoned and, if this is the case, to know whether this or these sensors are still capable of carrying out reliable measurements or if their degree of poisoning is such that it needs to be inactivated.

Yet, it would be desirable to be able to dispose of such a tool in order to optimise the performances of electronic noses and, particularly, bio-inspired electronic noses.

DESCRIPTION OF THE INVENTION

The invention precisely aims to remedy the shortcomings of the prior art by proposing, firstly, a method that makes it possible to determine simply and safely a potential poisoning of a sensor of an electronic nose by a volatile compound following a $n^{th}$ exposure of the sensor to a gaseous sample comprising at least this volatile compound, n being an integer greater than or equal to 1.

This method comprises at least the steps of:
a) eliminating the gaseous sample from the sensor after the exposure of the sensor to the gaseous sample;
b) measuring the baseline $B_n$ of the sensor after eliminating the gaseous sample;
c) calculating a poisoning indicator IE via formula:

$$IE = (B_n - B_{n-1}) - (f \times U_n)$$

wherein:
$B_{n-1}$ is the baseline of the sensor before the exposure of the sensor to the gaseous sample;
$U_n$ is the amplitude of the signal emitted by the sensor during its exposure to the gaseous sample;
f is a weighting parameter; and
d) comparing the poisoning indicator IE thus calculated with a threshold value S1;
whereby:
if IE is less than the threshold value S1, then the sensor is not poisoned; and
if IE is greater than or equal to the threshold value S1, then the sensor is poisoned.

In the foregoing and the following, "sensor" means an assembly that comprises:
* a sensitive portion that is disposed on a substrate and that is functionalised by one or more receptors capable of interacting physicochemically with at least one volatile compound, and
* a measuring system, typically called transducer, the function of which is to measure a variation of a physical quantity resulting from the receptor(s)/volatile compound physicochemical interaction and to convert this measurement into a measurable signal, it being understood that, in the case of a network of sensors as that which comprises an electronic nose, each of the sensors of this network may comprise its own measuring system or share with other sensors a measuring system that is common to them.

Moreover, "baseline" of a sensor means the intensity of the signal emitted by the sensor in the absence of any contact of the sensitive portion of this sensor with a volatile compound with which the sensor is likely to react.

As known per se, the step of eliminating the gaseous sample from the sensor, or step a), is advantageously performed by rinsing the sensor with a neutral gas, which may particularly be ambient air, dry air, moist air with controlled humidity, helium, dinitrogen, argon or carbon dioxide.

In accordance with the invention, the threshold value S1 is, preferably, equal to 0, in which case the weighting parameter f is positive and less than 1, preferably at most equal to 0.5. Even better, f is equal to 0.05.

Moreover,
A sensor that is poisoned by a volatile compound may:
* either still be functional, namely that it may still be used to perform one or more measurements because, although poisoned, it is not saturated by the volatile compound,

* or no longer be functional due to a saturation by the volatile compound.

In addition, the method of the invention also comprises, if IE is equal to or greater than the threshold value S1, the steps of:
e) calculating a functionality indicator IF of the sensor via formula:

$$IF = \frac{B_n - B}{p}$$

wherein:
B is a reference baseline;
p is a parameter representative of the working range of the sensor; and
f) comparing the functionality indicator IF thus calculated with a threshold value S2;
whereby:
if IF is less than the threshold value S2, then the sensor is still functional because not saturated by the volatile compound, and
if IF is greater than or equal to the threshold value S2, then the sensor is no longer functional because saturated by the volatile compound.

The expression "working range" of the sensor means in its usual acceptance, namely that it designates the interval of values of the physical quantity that must be measured by the sensor (such as a variation of reflectivity in the case of a surface plasmon resonance optical sensor) wherein the sensor is capable of providing reliable measurements. Any sensor has a working range that is indicated by its manufacturer.

In accordance with the invention, the baseline B is, preferably, the initial baseline $B_0$ of the sensor, that is to say the baseline that this sensor has:
either when new,
or when, after having switched on the electronic nose, performed the calibration tests recommended by its manufacturer and rinsed the sensor by means of a neutral gas for a time ranging from 30 seconds to 2 minutes and, typically, for 1 minute, no signal variation is observed for the sensor.

Moreover, p is, preferably, the upper limit, noted Γ, of the working range of the sensor.

As for the threshold value S2, it ranges, preferably, from 0.4 to 0.9 and, even better, is equal to 0.7.

In accordance with the invention, the receptor or receptors with which the sensitive portion of the sensor is functionalised are, preferably, biomolecules, that is to say molecules naturally present in living beings such as oligonucleotides, nucleic acids, carbohydrates, peptides, proteins, lipids, etc., or biomimetic molecules, that is to say molecules that imitate structurally and/or functionally the biological molecules.

Moreover, the volatile compound may be an organic compound, or VOC, or a inorganic compound such as ammonia, hydrogen sulphide, sulphur dioxide, etc.

In this regard, it is specified that the notion of VOC is defined by the Directive 1999/13/EC of the European Council of 11 Mar. 1999 in virtue of which:
a volatile organic compound is "any organic compound having at 293.15 K (i.e. 20° C.) a vapour pressure of 0.01 kPa (i.e. $9.87 \cdot 10^{-5}$ atm) or more, or having a corresponding volatility under the particular conditions of use" (see paragraph 17 of Article 2 of the Directive);

an organic compound is "any compound containing at least the element carbon and one or more of hydrogen, halogens, oxygen, sulphur, phosphorus, silicon or nitrogen, with the exception of carbon oxides and inorganic carbonates and bicarbonates" (see paragraph 16 of Article 2 of the Directive).

Thus, VOC are particularly, certain saturated or unsaturated acyclic hydrocarbons (ethane, propane, n-butane, n-hexane, ethylene, propylene, 1,3-butadiene, acetylene, etc.), certain saturated or unsaturated cyclic hydrocarbons (cyclopropane, cyclopentane, cyclohexane, etc.), certain aromatic hydrocarbons (benzene, toluene, xylenes, ethylbenzene, etc.), certain halogen hydrocarbons (dichloromethane, trichloromethane, chloroethane, trichloroethylene, tetrachloroethylene, etc.), certain alcohols (methanol, ethanol, 1-propanol, 2-propanol, ethylene glycol, propylene glycol, etc.), certain aldehydes (formaldehyde, acetaldehyde, propanal, 2-propenal (or acrolein), etc.), certain ketones (acetone, methyl ethyl ketone, 2-butanone, methyl vinyl ketone, etc.), certain esters (methyl acetate, ethyl acetate, isopropyl acetate, isoamyl butyrate, etc.), certain ethers (diethyl ether, ethylene glycol n-butyl ether, 1,4-dioxane, etc.), certain acids (acetic acid, propanoic acid, etc.), certain amines (ethylamine, dimethylamine, trimethylamine, diethylamine, amylamine, etc.), certain amides (dimethylformamide for example), certain thiols (methyl mercaptan or methanethiol, ethyl mercaptan or ethanethiol, etc.), certain nitriles (acetonitrile, acrylonitrile, etc.) as well as other compounds comprising a plurality of different chemical functions.

Another object of the invention is a computer program comprising instructions that, when the program is executed by a computer, lead the computer to implement the calculation and comparison steps of the method as defined above.

Another object of the invention is an electronic nose comprising a data processing unit configured to implement the calculation and comparison steps of the method as defined above.

Other features and advantages of the invention will become apparent from the additional description that follows and that is given with reference to the appended figures.

However, it goes without saying that this additional description is only given by way of illustration of the subject matter of the invention and shall under no circumstances be interpreted as a limitation of this subject matter.

DETAILED DESCRIPTION OF SPECIFIC EMBODIMENTS

Figure 1A:
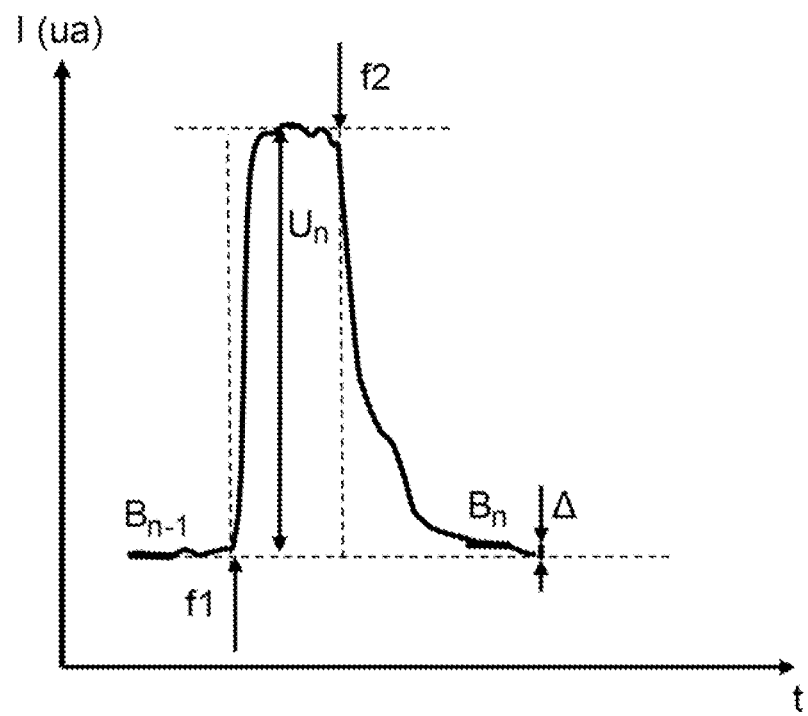
FIG. 1A illustrates an example of the profile that the signal emitted by a front electronic nose sensor has, during and after an exposure to a gaseous sample comprising a volatile compound with which the sensor is capable of reacting, in the absence of poisoning of the sensor by the volatile compound; in this figure, the intensity of the signal, noted I and expressed in arbitrary units (au) is indicated along the ordinate axis, whereas the time, noted t, is indicated along the abscissa axis.
Figure 1B:
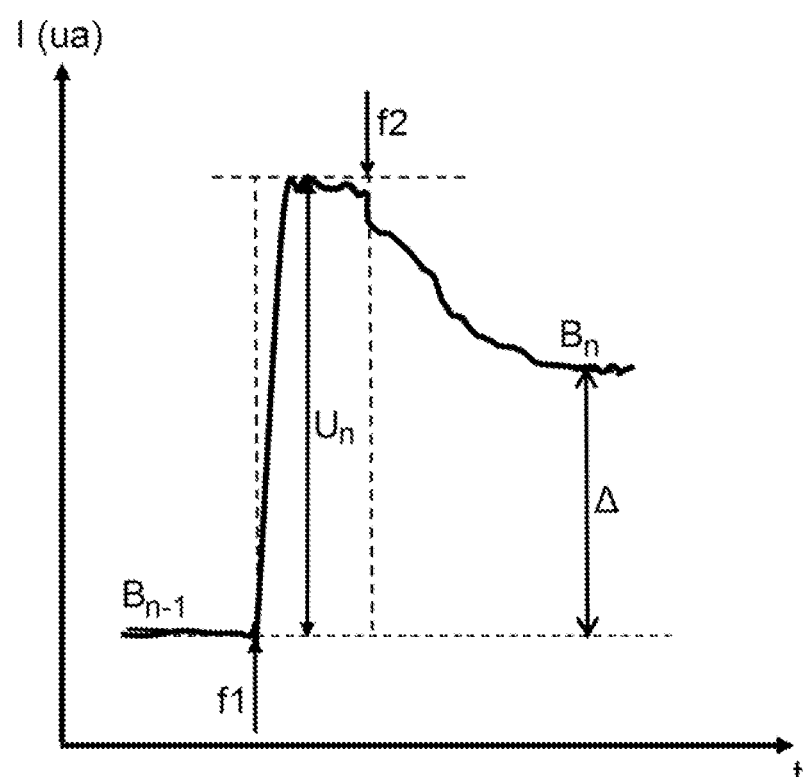
FIG. 1B illustrates an example of the profile that the signal emitted by a front electronic nose sensor has, during and after an exposure to a gaseous sample comprising a volatile compound with which the sensor is capable of reacting, in case of poisoning of the sensor by the volatile compound; in this figure, the intensity of the signal, noted I and expressed in arbitrary units (au) is indicated along the ordinate axis, whereas the time, noted t, is indicated along the abscissa axis.

I—Poisoning and Saturation of a Sensor by a Poisonous Volatile Compound:

Reference is made firstly to FIGS. 1A and 1B that each illustrate an example of the profile that the signal emitted by a front electronic nose sensor has, during and after a $n^{th}$ exposure to a gaseous sample comprising a volatile compound with which the sensor is capable of reacting, n being an integer greater than or equal to 1, in the absence of poisoning of the sensor by the volatile compound for FIG. 1A and in the case of a poisoning of the sensor by the volatile compound for FIG. 1B.

In these figures, the arrows f1 indicate the start of the exposure of the sensor to the gaseous sample, for example by injection of this sample into the chamber of the electronic nose, whereas the arrows f2 indicate the start of the elimination of the gaseous sample from the chamber of the electronic nose, for example by injection of a neutral gas (ambient air, dry air, nitrogen, argon, etc.) into this chamber.

As shown in FIGS. 1A and 1B, the sensor has, before the exposure of the gaseous sample, a baseline, noted $B_{n-1}$, which corresponds to the intensity of the signal that the sensor emits in the absence of any contact of its sensitive portion with a volatile compound with which it is likely to react.

The exposure of the sensor to the gaseous sample causes an immediate increase of the intensity of the signal emitted by the sensor. This intensity reaches a plateau at which it is maintained until the start of the elimination of the gaseous sample. The amplitude of the signal, noted $U_n$, is given by the difference between the intensity of the signal at the plateau and the baseline $B_{n-1}$.

Due to the elimination of the gaseous sample, the intensity of the signal emitted by the sensor drops until reaching a new baseline, noted $B_n$.

In the absence of poisoning of the sensor by the volatile compound, the baseline $B_n$ is identical to the baseline $B_{n-1}$ or, as illustrated in FIG. 1A, only differs from the baseline $B_{n-1}$ by a low delta (Δ).

On the other hand, as illustrated in FIG. 1B, a poisoning of the sensor by the volatile compound results in a delta (Δ) between the baselines $B_n$ and $B_{n-1}$ that is much greater than that observed in the absence of poisoning of the sensor, this Δ being able to go up to 100% of the amplitude $U_n$ of the signal emitted by the sensor during its exposure to the gaseous sample.

Figure 2:
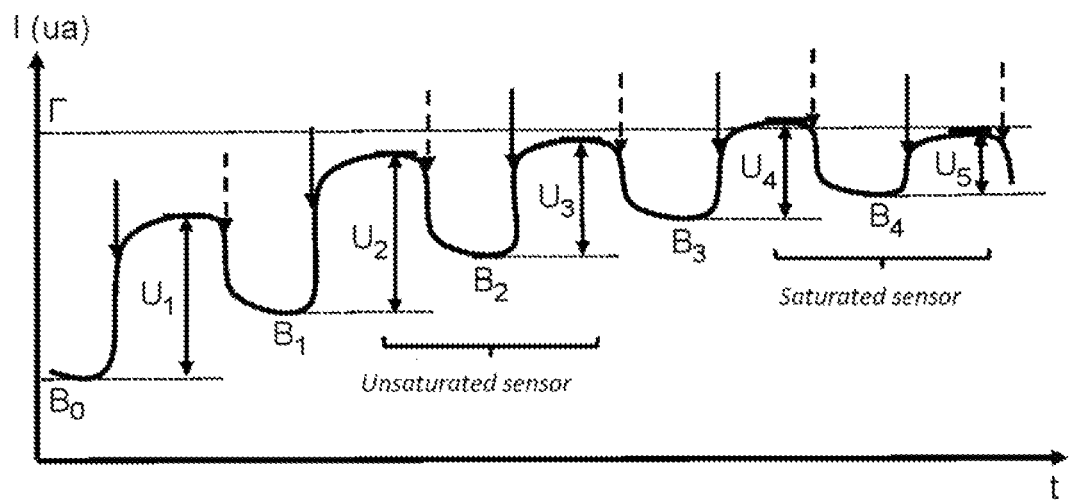
FIG. 2 illustrates an example of the profile that the signal emitted by an electronic nose sensor has when it is subjected to a series of exposures to gaseous samples comprising a volatile compound with which the sensor is capable of reacting, in case of repeated poisoning of the sensor by the volatile compound up to the saturation of this sensor; in this figure, the intensity of the signal, noted I and expressed in arbitrary units (au) is indicated along the ordinate axis, whereas the time, noted t, is indicated along the abscissa axis.

Reference is now made to FIG. 2 that illustrates an example of the profile that the signal emitted by an electronic nose sensor has when it is subjected to a series of exposures to gaseous samples comprising a volatile compound with which the sensor is capable of reacting, in case of repeated poisoning of the sensor by the volatile compound up to the saturation of this sensor.

In an arbitrary and purely illustrative manner, the exposures of the sensor are five in number in FIG. 2.

In this figure, the directional arrows in solid lines indicate the start of the exposures of the sensor to gaseous samples whereas the directional arrows in dotted lines indicate the start of the elimination of the gaseous samples from the chamber of the electronic nose.

The baseline that the sensor has initially, that is to say before the first exposure of the sensor, is noted $B_0$, whereas the baseline that the sensor has after each of the five exposures is noted respectively $B_1$, $B_2$, $B_3$, $B_4$ and $B_5$.

In a similar manner, the amplitude of the signal emitted by the sensor during each of the five exposures is noted respectively $U_1$, $U_2$, $U_3$, $U_4$ and $U_5$.

The dotted line noted $\Gamma$ indicates, for its part, the upper limit of the working range of the sensor, this working range corresponding to the interval of values of the physical quantity that must be measured by the sensor wherein the sensor is capable of providing reliable measurements.

By allocating the value 0 to the baseline $B_0$, the sensor is considered as functional as long as the physical quantity measured varies between 0 and $\Gamma$ or, in other terms, the signal emitted by the sensor falls within the interval $[0; \Gamma]$.

As shown in FIG. 2, successive exposures of a sensor to gaseous samples comprising a poisonous volatile compound result in a progressive increase, exposure after exposure, of the baseline of the sensor with, consequently, a reduction of the amplitude of the signal emitted by the sensor during the exposures.

Thus, for example, $U_2$ is equal to 90% of $U_1$; $U_3$ is equal to 60% of $U_1$; $U_4$ is equal to 40% of $U_1$ whereas $U_5$ only represents 20% of $U_1$.

The amplitude of the signal emitted by the sensor during the first three exposures falls within the interval $[0; \Gamma]$, which means that, although the sensor is poisoned (given the $\Delta$ existing between $B_1$ and $B_0$), it is still functional.

On the other hand, the signal emitted by the sensor during the $4^{th}$ exposure leaves the interval $[0; \Gamma]$, which means that the sensor is no longer functional because saturated by the poisonous volatile compound and that the measurements provided by this sensor are no longer reliable.

It is precisely to prevent a sensor and, hence, the electronic nose that comprises this sensor from providing unreliable measurements that it is proposed according to the invention:
- on the one hand, to determine whether a sensor is or is not poisoned by a volatile compound following an exposure to a gaseous sample comprising this volatile compound by calculating a poisoning indicator IE and by comparing this indicator with a threshold value S1; and
- on the other hand, in the case where it results from the preceding calculation that the sensor is poisoned, to determine whether the sensor is still functional or not by calculating a functionality indicator IF and by comparing this indicator with a threshold value S2.

II—Poisoning Indicator IE of a Sensor:

If reference is made again to FIGS. 1A and 1B, the poisoning indicator IE corresponds to the $\Delta$ between the baselines $B_n$ and $B_{n-1}$ from which is subtracted the amplitude $U_n$ of a signal emitted by the sensor while it is exposed to the gaseous sample, this amplitude being weighted by a weighing parameter f.

In other terms, IE is equal to: $(B_n - B_{n-1}) - (f \times U_n)$.

Thus, if IE is less than the threshold value S1, then the sensor is not poisoned whereas, if IE is greater than or equal to the threshold value S1, then the sensor is poisoned.

The threshold value S1 is preferably equal to 0.

The weighting parameter f is then positive and less than 1, advantageously at most equal to 0.5. Even better, f is equal to 0.05.

The profile shown in FIG. 1A is typically a profile for which, for a weighting parameter f of 0.05, IE is less than 0, thus marking an absence of poisoning of the sensor by the volatile compound, whereas the profile shown in FIG. 1B is typically a profile for which, with the same weighting parameter, IE is greater than 0, marking, on the contrary, a poisoning of the sensor by the volatile compound.

If reference is made to FIG. 2, the poisoning indicator IE of the sensor may be measured from the first exposure of this sensor to a gaseous sample, in which case IE is equal to: $(B_1 - B_0) - (f \times U_1)$ and, if we take $f = 0.05$, then IE is equal to $(B_1 - B_0) - 0.05 U_1$.

III—Functionality Indicator IF of a Poisoned Sensor:

The functionality indicator IF corresponds to the $\Delta$ between the baseline $B_n$—of which it is reminded that this concerns the baseline to which the sensor returns following an exposure to a gaseous sample—and a reference baseline, noted B, divided by a parameter, noted p, representative of the working range of the sensor.

In other terms, IF is equal to: $(B_n - B)/p$.

Thus, if IF is less than the threshold value S2, then the sensor, although poisoned, is still functional and may still be used for at least one measurement whereas if IF is greater than or equal to the threshold value S2, then the sensor is saturated by the volatile compound and may no longer be used, at least temporarily.

The baseline B is, preferably, the initial baseline, noted $B_0$ of the sensor.

The parameter p is, preferably, the upper limit of the working range of the sensor.

The threshold value S2 is, for its part, between 0.4 and 0.9 and, preferably equal to 0.7.

If reference is made again to FIG. 2, it is noted that, for $p = \Gamma$ and $S2 = 0.7$, the functionality indicator obtained after the first exposure of the sensor to a gaseous sample, namely $IF = (B_1 - B_0)/\Gamma$, is less than 0.7 or, in other words, at 70% of the interval $[0; \Gamma]$.

The same applies for the functionality indicator obtained after the second exposure of the sensor to a gaseous sample, namely $IF = (B_2 - B_0)/\Gamma$. The sensor is therefore still functional after this second exposure.

On the other hand, the functionality indicator obtained after the third exposure of the sensor to a gaseous sample, namely $IF = (B_3 - B_0)/\Gamma$, is greater than 0.7, which means that the sensor is no longer capable of carrying out a new reliable measurement.

The same applies a fortiori for the functionality indicator obtained after the fourth and fifth exposures of the sensor to a gaseous sample.

Figure 3:
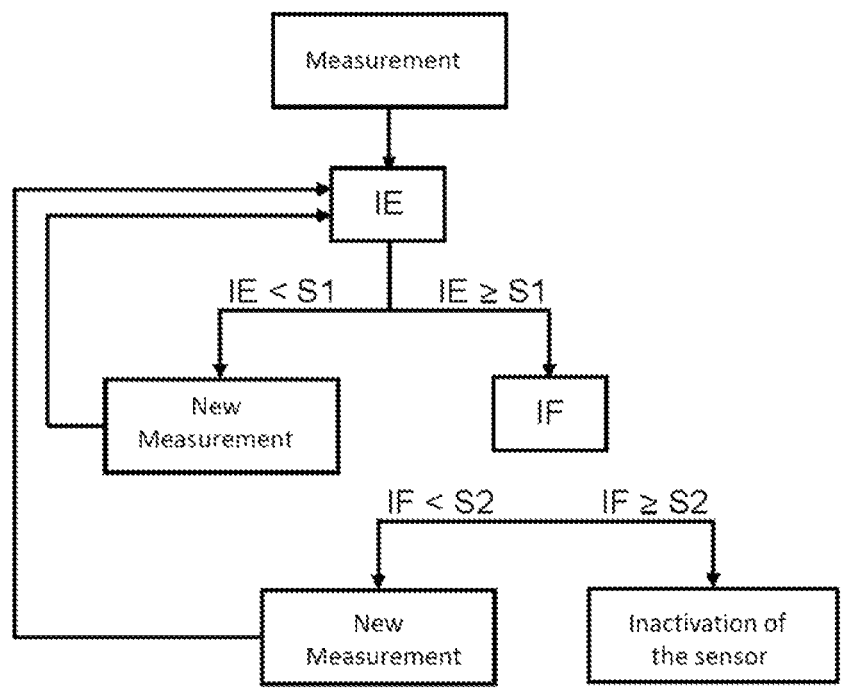
FIG. 3 illustrates, in the form of a decision tree, an example of implementation of the method of the invention in an electronic nose.

IV—Diagram of One Implementation of the Method of the Invention in an Electronic Nose:

Reference is made to FIG. 3 that illustrates, in the form of a decision tree, an example of implementation of the method of the invention in an electronic nose.

The starting point of this decision tree is a measurement that has been performed by a sensor during an exposure of this sensor to a gaseous sample comprising a volatile compound with which this sensor is likely to react.

This exposure is preferably but is not necessarily the first exposure of the sensor to a gaseous sample comprising the volatile compound.

Following the measurement carried out by the sensor, the poisoning indicator IE of the sensor is calculated and compared with the threshold value S1 by the data processing unit of the electronic nose.

If IE is less than the threshold value S1, then the electronic nose indicates that the sensor is capable of carrying out a new reliable measurement.

If IE is greater than or equal to the threshold value S1, then the data processing unit of the electronic nose calculates the functionality indicator IF of the sensor and compares this indicator with the threshold value S2.

If IF is greater than or equal to the threshold value S2, then the electronic nose indicates that the sensor is no longer able to carry out reliable measurements and the sensor is inactivated and intended to be replaced.

If IF is less than the threshold value S2, then the electronic nose indicates that the sensor is capable of carrying out a new reliable measurement.

If a new measurement is carried out, then the data processing unit of the electronic nose recalculates, at the end of this measurement, the poisoning indicator IE of the sensor and compares it again with the threshold value S1 and, depending on the case, recalculates the functionality indicator IF and compares it with the threshold value S2. This diagram is reproduced as long as the electronic nose does not indicate that the sensor is no longer able to carry out a reliable measurement.

REFERENCES CITED

S. Brenet et al., *Analytical Chemistry* 2018, 90, 9879-9887
French patent application 3 071 061

What is claimed is:

1. A method for determining a potential poisoning of a sensor of an electronic nose by a volatile compound following a $n^{th}$ exposure of the sensor to a gaseous sample comprising at least the volatile compound, n being an integer greater than or equal to 1, comprising at least the steps of:
    a) eliminating the gaseous sample from the sensor after the exposure of the sensor to the gaseous sample;
    b) measuring a baseline $B_n$ of the sensor after eliminating the gaseous sample;
    c) calculating a poisoning indicator IE via formula:

$$IE = (B_n - B_{n-1}) - (f \times U_n)$$

wherein:
    $B_{n-1}$ is a baseline of the sensor before the exposure of the sensor to the gaseous sample;
    $U_n$ is an amplitude of a signal emitted by the sensor during its exposure to the gaseous sample;
    f is a weighting parameter; and
    d) comparing the poisoning indicator IE thus calculated with a threshold value S1;
    whereby:
        if IE is less than the threshold value S1, then the sensor is not poisoned; and
        if IE is greater than or equal to the threshold value S1, then the sensor is poisoned;

and further comprising, if IE is equal to or greater than the threshold value S1, the steps of:
    e) calculating a functionality indicator IF of the sensor via formula:

$$IF = \frac{B_n - B}{p}$$

wherein:
    B is a reference baseline;
    p is a parameter representative of a working range of the sensor; and
    f) comparing the functionality indicator IF thus calculated with a threshold value S2;
    whereby:
        if IF is less than the threshold value S2, then the sensor is still functional; and
        if IF is greater than or equal to the threshold value S2, then the sensor is no longer functional.

2. The method of claim 1, wherein the threshold value S1 is equal to 0.

3. The method of claim 1, wherein f is greater than 0 and less than 1.

4. The method of claim 1, wherein B is an initial baseline of the sensor.

5. The method of claim 1, wherein p is an upper limit of the working range of the sensor.

6. The method of claim 1, wherein the threshold value S2 ranges from 0.4 to 0.9.

7. The method of claim 1, wherein the sensor comprises a sensitive portion that is functionalised by one or more receptors capable of interacting physicochemically with the volatile compound, and wherein the receptor or receptors are selected from biological molecules and biomimetic molecules.

8. A non-transitory computer-readable medium having instruction stored thereon that, when executed by a processor, leads the processor to implement steps c) and d) of the method of claim 1.

9. An electronic nose, comprising a data processing unit configured to implement steps c) and d) of the method of claim 1.

10. The method of claim 1, wherein f is at most equal to 0.5.

11. The method of claim 1, wherein f is equal to 0.05.

12. The method of claim 1, wherein the threshold value S2 is equal to 0.7.

13. A non-transitory computer-readable medium having instruction stored thereon that, when executed by a processor, leads the processor to implement the steps c), d, e) and f) of the method of claim 1.

14. An electronic nose, comprising a data processing unit configured to implement steps c), d), e) and f) of the method of claim 1.

* * * * *